US007008620B2

(12) United States Patent
Sun et al.

(10) Patent No.: US 7,008,620 B2
(45) Date of Patent: Mar. 7, 2006

(54) DEPILATORY COMPOSITIONS AND ARTICLES AND THE USE THEREOF

(75) Inventors: Ying Sun, Belle Mead, NJ (US); Diana L. Friscia, Fairless Hills, PA (US); Vipul Dave, Hillsborough, NJ (US); Elvin R. Lukenbach, Flemington, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 486 days.

(21) Appl. No.: 10/261,321

(22) Filed: Sep. 30, 2002

(65) Prior Publication Data
US 2004/0062735 A1    Apr. 1, 2004

(51) Int. Cl.
A45D 19/00    (2006.01)
A61K 7/06    (2006.01)
A61K 7/15    (2006.01)

(52) U.S. Cl. .......................................... 424/73; 424/400

(58) Field of Classification Search .................. 424/73
See application file for complete search history.

(56) References Cited

U.S. PATENT DOCUMENTS

| 3,341,418 A | 9/1967 | Moses et al. |
| 4,011,878 A | 3/1977 | Abegg et al. |
| 4,115,293 A | 9/1978 | Schoenholz et al. |
| 4,121,904 A | 10/1978 | Schamper |
| 4,152,784 A * | 5/1979 | McGalliard .................. 2/239 |
| 4,206,068 A | 6/1980 | Davis |
| 4,971,782 A | 11/1990 | Rudy et al. |
| 5,645,428 A | 7/1997 | Yarborough |
| 5,713,738 A | 2/1998 | Yarborough |
| 5,848,569 A | 12/1998 | Anderson et al. |
| 5,891,453 A | 4/1999 | Sagel et al. |
| 5,894,017 A | 4/1999 | Sagel et al. |
| 5,989,569 A | 11/1999 | Dirksing et al. |
| 6,045,811 A | 4/2000 | Dirksing et al. |
| 6,096,328 A | 8/2000 | Sagel et al. |
| 6,162,055 A | 12/2000 | Montgomery et al. |
| 6,254,388 B1 | 7/2001 | Yarborough |
| 6,270,783 B1 | 8/2001 | Slavtcheff et al. |
| 6,287,580 B1 | 9/2001 | Gott et al. |
| 2002/0006388 A1 | 1/2002 | Sagel et al. |
| 2002/0012685 A1 | 1/2002 | Sagel et al. |
| 2002/0061329 A1 | 5/2002 | Leaderman |
| 2002/0094321 A1 | 7/2002 | Gamier et al. |

FOREIGN PATENT DOCUMENTS

| DE | 1000 28 848 A | 1/2002 |
| EP | 0 273 202 A2 | 7/1988 |
| EP | 1 224 925 A | 7/2002 |
| GB | 521 215 | 6/1939 |
| WO | WO 00/41673 A1 | 7/2000 |
| WO | WO 01/12147 A1 | 2/2001 |
| WO | WO 01/68045 A | 9/2001 |

OTHER PUBLICATIONS

International Cosmetic Ingredient Dictionary and Handbook, Seventh Edition, vol. 2, Wenninger et al., 1997, pp. 1653, 1655-1656, 1612-1613, 1654-1662, 1626.
Kirk-Othmer Encyclopedia of Chemical Technology, Fourth Edition, vol. 18, John Wiley & Sons, 1996, pp. 202-210.
Cosmetics-Science and Technology, vol. 2, John Wiley & Sons, 1972, pp. 39-72.

* cited by examiner

Primary Examiner—Thurman Page
Assistant Examiner—Nabila Ebrahim

(57) ABSTRACT

The present invention relates to a composition or article containing at least one oxidizing agent and at least one reducing agent, wherein at least one of the at least one reducing agent is a depilatory agent, the equivalent ratio of the at least one oxidizing agent to the at least one reducing agent is less than 1:1, and the article is exothermic when wet with water, and the use thereof to remove hair from the skin.

20 Claims, No Drawings

DEPILATORY COMPOSITIONS AND ARTICLES AND THE USE THEREOF

FIELD OF THE INVENTION

The present invention relates to a substantially dry composition or article and the uses thereof to remove hair from the skin.

BACKGROUND OF THE INVENTION

Depilatory agents have been used for many years to remove unwanted hair from skin on the human body. The most common depilatory agents are thioglycolates, in particular alkaline earth metal thioglycolates such as calcium thioglycolate. A slight excess of alkalinity is often included in the composition in order to provide a reservoir of alkalinity to help maintain the alkalinity of the composition at a desired pH value, generally in a pH range of at least 10, such as about 12 to about 12.5. The foregoing are disclosed in the U.S. Pat. No. 4,121,904 and in *Cosmetics—Science and Technology* (edited by Balsam et al), Volume 2, John Wiley & Sons, Inc., 1972, New York, page 39–72.

Such depilatories are most commonly marketed in the form of creams or pastes. Following application to the skin from about 5 to about 15 minutes, these agents effectively remove the unwanted hair, generally without irritation of the human skin. These agents are also readily wiped or washed off, along with the degraded unwanted hair, with water.

The present invention relates to a substantially dry composition or article containing at least one oxidizing agent and at least one reducing agent and the uses thereof to remove hair from the skin. The following is a summary of various U.S. patents that disclose the use of oxidizing and reducing agents.

U.S. Pat. No. 3,341,418 describes a two-part aqueous composition in which the parts are mixed immediately before or during use with simultaneous evolution of heat. One part contains a reducing agent (e.g., thiourea) and the second part contains an oxidizing agent (e.g., hydrogen peroxide). These compositions are used for cosmetic applications such as skin and hair care, and in particular for shaving preparations.

U.S. Pat. No. 4,011,878 describes a process for permanently waving hair using a self-heating composition containing two aqueous components: one component containing a water-soluble sulfite, metabisulfite or bisulfite and thiourea, and a second component containing hydrogen peroxide. The two components are mixed prior to use, resulting in an exothermic reaction.

U.S. Pat. No. 4,206,068 discloses cleaning compositions for drains using oxidizing and reducing agents and an alkali metal hydroxide. To prevent a premature reaction of the oxidizing and reducing agents, the ingredients are kept separate until actual utilization for drain cleaning purposes.

U.S. Pat. No. 6,287,580 describes a self-heating cosmetic composition that includes a skin conditioning agent and a redox system based on iron powder (e.g., elemental iron, iron oxides and ferrous salts) and a high surface area catalyst (e.g., charcoal, alumina, clays, silica). The compositions are taught in different forms such as lotions, creams, emulsions, ointments, and pad applied formulations. The system is activated with moisture and air.

SUMMARY OF THE INVENTION

In one aspect, the present invention relates to a substantially dry article including an insoluble substrate, at least one oxidizing agent, and at least one reducing agent, wherein at least one of the at least one reducing agent is a depilatory agent, the equivalent ratio of the at least one oxidizing agent to the at least one reducing agent is less than 1:1, and the article is exothermic when wet with water. In another aspect, the present invention features a method of removing hair from the skin by applying to the hair the above article, wherein the article is wet with water prior to, during or after said application.

In another aspect, the present invention features a method of removing hair from the skin by wetting a composition with water prior to, during, or after application of the composition to the hair, wherein the composition includes at least one oxidizing agent and at least one reducing agent, wherein at least one of the at least one reducing agent is a depilatory agent, the equivalent ratio of the at least one oxidizing agent to the at least one reducing agent is less than 1:1, and the composition is exothermic when wet with water.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Whenever used, any percentage is weight by weight (w/w) unless otherwise indicated.

The article or composition is preferably substantially dry. As used herein, "substantially dry" means that the article or composition contains less than about 10 percent, preferably less than about 5 percent, and more preferably less than about 1 percent by weight of unbound water, based on the total weight of the article or composition. In one embodiment, the article or composition contains less than less than about 10 percent, preferably less than about 5 percent, and more preferably less than about 1 percent by weight of total water (e.g., bound and unbound water), based on the total weight of the article or composition.

Water-Insoluble Substrate

In one embodiment, the article of the present invention includes a water-insoluble substrate. By "water insoluble" is meant that the substrate, upon immersion in distilled water at 25° C., does not readily dissolve in or readily break apart. The water-insoluble substrate may, however, be disintegrated and/or dissolved slowly, e.g., over a period of several hours up to several days.

A wide variety of materials can be used as the substrate. Examples of suitable substrates include, but are not limited to, nonwoven substrates, woven substrates, hydroentangled substrates, air entangled substrates, natural sponges, synthetic sponges, polymeric netted meshes, and the like. In one embodiment, the substrate is an absorbent or a porous material.

The substrate may be flushable. As used herein, by "flushable" is meant that the substrate will pass through at least 10 feet of waste pipe in two toilet flushes. The material may also be biodegradable.

In one embodiment, the substrate contains a nonwoven material. By "nonwoven" is meant that the substrate, or a layer of the substrate, is comprised of fibers which are not woven into a fabric but rather are formed into a sheet, mat, or pad layer. The fibers can either be random (i.e., randomly aligned) or they can be carded (i.e. combed to be oriented in primarily one direction). Furthermore, the nonwoven substrate can be composed of a combination of layers of random and carded fibers.

Nonwoven substrates may be comprised of a variety of natural and/or synthetic materials. By "natural" is meant that the materials are derived from plants, animals, insects or byproducts of plants, animals, and insects. By "synthetic" is meant that the materials are obtained primarily from various man-made materials or from natural materials which have been further altered. Nonlimiting examples of natural materials useful in the present invention are silk fibers, keratin fibers (such as wool fibers, camel hair fibers) and cellulosic fibers (such as wood pulp fibers, cotton fibers, hemp fibers, jute fibers, flax fibers, and mixtures thereof).

Examples of synthetic materials include, but are not limited to, those selected from the group containing of acetate fibers, acrylic fibers, cellulose ester fibers, modacrylic fibers, polyamide fibers, polyester fibers, polyolefin fibers, polyvinyl alcohol fibers, rayon fibers, polyurethane foam, and mixtures thereof.

Substrates made from natural and synthetic materials useful in the present invention can be obtained from a wide variety of commercial sources such as Freudenberg & Co. (Durham, N.C. USA), BBA Nonwovens (Nashville, Tenn. USA), PGI Nonwovens (North Charleston, S.C. USA), Buckeye Technologies/Walkisoft (Memphis, Tenn. USA), and Fort James Corporation(Deerfield, Ill. USA).

Methods of making nonwoven substrates are also well known in the art. Such methods include, but are not limited to, air-laying, water-laying, meltblowing, spinbonding, or carding processes. The resulting substrate, regardless of its method of production or composition, is then subjected to at least one of several types of bonding operations to anchor the individual fibers together to form a self-sustaining web. The nonwoven substrate can be prepared by a variety of processes including hydroentanglement, thermally bonding, and combinations of these processes. Moreover, the substrates can consist of a single layer or multiple layers. In addition, a multilayered substrate can include film layer(s) (e.g., apertured or non-apertured film layers) and other nonfibrous materials.

In one embodiment, the substrate is paper based. The materials for these substrates are made almost exclusively of cellulose-based fibres or filaments from plant cellular sources (pulp). These can be available from fresh woodshavings or from recycled material (recycled paper).

If the substrate is to be used in a cleansing article (e.g., a facial or body wipe), high wet strength or firmness of the nonwoven material may be a desirable attribute. This can be achieved, for example, by the addition of binding materials, such as wet strength resins, or the material may be made of staple fibers, e.g. based on cotton, wool, linen and the like. Examples of wet strength resins include, but are not limited to, vinyl acetate-ethylene (VAE) and ethylene-vinyl chloride (EVCL) Airflex emulsions (Air Products, Lehigh, Pa.), Flexbond acrylic polymers (Air Products, Lehigh, Pa.), Rhoplex ST-954 acrylic binder (Rohm and Haas, Philadelphia, Pa.), and Ethylene-vinyl acetate (EVA) emulsion (DUR-O-SET® by National Starch Chemicals, Bridgewater, N.J.). The amount of binding material in the substrate may range from about 5% to about 20%, by weight, of the substrate.

Nonwoven materials of increased strength can be obtained by using the so-called spunlace or hydro-entanglement technique. In this technique, the individual fibers are twisted together so that an acceptable strength or firmness is obtained without the need to use binding materials. The advantage of the latter technique is the excellent softness of the nonwoven material.

Additives may also be added in order to increase the softness of the substrate. Examples of such additives include, but are not limited to, polyols such as glycerol, propylene glycol and polyethylene glycol, phthalate derivatives, citric esters, surfactants such as polyoxyethylene (20) sorbitan esters, and acetylated monoglycerides.

In one embodiment, the substrate is a woven substrate. Examples of woven substrates include, but are not limited to, woven cotton and polyester substrates. Examples of woven substrates include, but are not limited to, towels such a bath or hand towels and articles of clothing such as socks, mittens, gloves, and hats.

In one embodiment, the substrate is an open-cell foam, such as a sponge sheet made of a synthetic polymer or natural materials.

In one embodiment, the substrate has a basis weight from about 10 $g/m^2$ to about 80 $g/m^2$, preferably from about 30 to about 70 $g/m^2$ and more preferably from about 40 to about 60 $g/m^2$.

In one embodiment, the substrate is in the shape of a flat sheet such as a wipe, a towlette, a towel, or the like. The shape of such substrate may be circular, oval, square, or rectangular. The size of the longest diameter such substrates may from about 2 inches to about 4 feet, such as from about 4 inches to about 2 feet. In one embodiment, the substrate is in the shape of sponge or a puff.

Oxidizing and Reducing Agents

In one embodiment, the article or composition of the includes at least one oxidizing agent and at least one reducing agent. Suitable oxidizing agents for the article or composition include, but are not limited to, alkali metal salts of perborates, persulfates, carbonate-peroxides and peroxides such as sodium perborate monohydrate, ammonium persulfate, sodium persulfate, potassium persulfate, sodium carbonate peroxide, benzoyl peroxide, calcium peroxide, magnesium peroxide, carbamide peroxide, and hydrogen peroxide. An anhydrous form of hydrogen peroxide is available from International Specialty Products (Wayne, N.J.) in the form of a complex of pharmaceutical grade poly(vinyl pyrrolidone) and hydrogen peroxide. Other suitable peroxides include those summarized in the "Kirk-Othmer Encyclopedia of Chemical Technology", Fourth Edition, J. I. Kroschwitz and M. Howe-Grant (Editors), Volume 18, pages 202–210 (John Wiley & Sons, 1996). Other oxidizing agents are recited in the International Cosmetic Ingredient Dictionary and Handbook, eds. Wenninger et al., p. 1653 (The Cosmetic, Toiletry, and Fragrance Association, $7^{th}$ Ed. 1997) (hereinafter the "INCI Handbook").

Suitable reducing agents include, but are not limited to, thiourea, salts (such as sodium salts) of thiosulfate, sulfite, bisulfite, metabisulfite, borohydride, and hypophosphite, ascorbic acid and salts, esters, and derivatives thereof (e.g., ascorbyl palmitate and ascorbyl polypeptide), and tocopherols and salts, esters, and derivatives thereof (e.g., tocopherol acetate). Other reducing agents are listed on pages 1655–56 of the INCI Handbook.

In one embodiment, the reducing agent is a depilatory agent. What is meant by a "depilatory agent" is a compound capable of removing or destroying hair, such as a compound capable of reacting with disulfide bonds of keratin. Examples of such depilatory agents include, but are not limited to, (i) compounds containing one or more thiol groups, such as thiol containing amino acids, and (ii) sulfides. Nonlimiting examples of thiol containing compounds include thioglycolic acid, thioethylene glycol, thioglycerol, thioethanol, thioactic acid, thiosalicylic acid and salts thereof (e.g., calcium, sodium, strontium, potassium, ammonium, lithium, magnesium, and other metal salts). Nonlimiting examples of thio-containing amino acids or their derivatives include L-cysteine, D-cysteine, DL-cysteine, N-acetyl-L-cysteine, DL-homocysteine, N-carbamoyl cysteine, glutathion, and cysteamine, and salts and esters thereof (e.g., methyl and ethyl esters). Nonlimiting examples of sulfides include calcium sulfide, sodium sulfide, potassium sulfide, lithium sulfide, and strontium sulfide.

In one embodiment, the pH value for the exothermic depilatory article or composition containing a thioglycolate or sulfide is preferably greater than about pH 9, and more preferably, greater than about pH 10. In one embodiment, the pH value for the exothermic depilatory article or composition containing a thio-containing amino acids or their derivative is preferably lower than about pH 7, and more preferably, lower than about pH 5.

The amount of oxidizing agent(s) and reducing agent(s) on an article will vary, depending on the size of the substrate, the oxidizing and reducing agents used, and the desired maximum temperature and duration of the exothermic reaction. In one embodiment, the total amount of oxidizing agent(s) and reducing agent(s), independently, is from about 0.005 g to about 0.5 g per square inch of the substrate.

The amount of oxidizing agent(s) and reducing agent(s) in the composition will also vary, depending on the oxidizing and reducing agents used and the desired maximum temperature and duration of the exothermic reaction. In one embodiment, the total amount of oxidizing agent(s) and reducing agent(s), independently, is from about 0.01 to about 30%, by weight, of the composition, such as from about 0.1% to about 20% (e.g., about 1% to about 10%).

To initiate the exothermic reaction, the composition or article must be wet with water, e.g., water must come in contact with the oxidizing and reducing agents. The water may be added prior to application (e.g., wetting the article with tap water just prior to use such as less than about five minutes, preferable less than about one minute, prior to use), during application (e.g., applying the article or composition to water on the skin, hair, or teeth), or after application (e.g., skin perspiration being absorbed into the composition or article).

In one embodiment, the equivalent ratio of oxidizing agent(s) to reducing agents(s) in the composition or the article, ranges from about 1:20 to about 20:1, such as from about 1:10 to about 10:1. What is meant by an "equivalent" of an oxidizing or reducing agent is the mass of such substance that will donate or accept one mole of electrons in an oxidation-reduction reaction. For instance, hydrogen peroxide donates two electrons per mole, so its oxidative equivalent is half its molar mass. Sodium sulfite is oxidized by acceptance of two electrons, so its reduction equivalent is half its molar mass. The term "equivalent ratio" refers to the ratio of the equivalents (e.g., of the oxidizing agent(s) to reducing agent(s) in the composition or article), thus factoring in the valency of multi-electron oxidants and reductants for the purposes of outlining desirable excesses of one or the other in practicing this invention.

In one embodiment, the article or composition is used to bleach or whiten the skin, hair, or teeth. In such a case, excess amount of oxidizing agent(s) is desired. Thus, the equivalent ratio of oxidizing agent(s) to reducing agent(s) may range from about 1.1:1 to about 20:1 such as from about 1.5:1 to about 10:1. In another embodiment, the article or composition is used to remove hair. In such a case, excess amount of reducing agent(s) is desired. Thus, the equivalent ratio of oxidizing agent(s) to reducing agent(s) may range from about 1:1.1 to about 1:20 such as from about 1:1.5 to about 1:10.

The target temperature range for the skin-contacting surface of the substrate is between about 30° to about 80° C. (e.g., between about 35° C. to 50° C.). In general, if the application duration is short (e.g., less than 10 minutes), the operating temperature may be at the higher end of the above temperature range. However, if the application duration is longer, a lower operating temperature (e.g., less than 42° C. is preferred to avoid heat-related tissue injury for prolonged skin exposure to the composition or article).

Addition of Water-soluble Polymers

In one embodiment, the reducing agent(s) and/or oxidizing agent(s) are in contact with a water-soluble polymer(s). The polymer(s) may be intermixed with or coat the surface of the reducing agent(s) and/or oxidizing agent(s). The presence of the water-soluble polymer may assist in preventing the pre-mature activation of the agents and/or to prevent the agents from directly contacting the skin or eyes of the user. Nonlimiting examples of such water-soluble polymer materials include polyethylene glycols ("PEGs") such as PEG-32 (Carbowax 1450) and PEG-765 (Carbowax 3350) from Union Carbide (Union Carbide, Midland, Mich.), polyethylene oxides such as PEG-2M (Polyox WSRN-10) and PEG-5M (Polyox WSRN-80) from Amerchol (Edison, N.J.), polyvinyl alcohols such as PVAXX resins C-20 and W-20 (Mitsui Plastics, White Plains, N.Y. USA), cellulose ethers such as hydroxypropyl cellulose, polyvinylpyrrolidone and copolymers of vinyl pyrrolidone such as coplymers of vinyl pyrrolidone and vinyl acetate such as PLASDONE S-630 (ISP, Wayne, N.J., USA), and mixtures thereof.

The weight ratio of water-soluble polymer(s) to the reducing agents(s) and/or oxidizing agents will depend on the type of polymers and agents used and the desired speed of the onset and/or duration of the exothermic reaction. In one embodiment, the weight ratio of water-soluble polymer(s) to the reducing agents(s) and/or oxidizing agent(s) is from about 1:1 to about 100:1, such as from about 2:1 to about 50:1.

Configurations of the Exothermic Article

The article of the invention may constitute a single layer substrate or a multi-layer substrate. In one embodiment, the substrate layer(s) containing the oxidizing and reducing agent(s) are enclosed in a porous, hydrophobic layer, which allows water to be absorbed into the substrate layer(s). In one embodiment, the hydrophobic layer is made of polyethylene. In one embodiment, the article has an insulating layer on the surface of article, e.g., for the purpose of either reducing heat loss or prolonging the heating benefit of the article. The insulating layer may be of a microporous nature such as a close-cell foam (e.g., a polethylene or polyurethane foam) or open-cell foam with a water impermeable polymer layer on one or both sides of the membrane.

The reducing agent and/or oxidizing agent can be added to the substrate during or after its preparation. For example, if the substrate is a nonwoven material, the agents can be incorporated into the substrate during the spinning or the conversion process to make the nonwoven substrate from fibers. Other approaches include, but are not limited to, dispersing the agents in the spin finish during the fiber spinning process or adding the agents by uniformly coating them onto the substrate.

Alternatively, the oxidizing agent may be incorporated into one layer of the substrate, while the reducing agent is incorporated into another layer of the substrate. The two layers are then overlayed together to form a dual-layer exothermic article. A multi-layer article can be fabricated in a similar manner with alternating layers containing respective oxidizing and reducing agents.

In one embodiment, the oxidizing and reducing agents are contained between two or more substrate layers. In one embodiment, the substrate layers are bound together (e.g., by heat, glue, or pressure) such that the bonded regions form one or more compartments between the layers to contain the oxidizing agent or reducing agent. In one embodiment, the article contains at least two layers that are bound together to create multiple compartments between the layers and the oxidizing agent(s) and reducing agents(s) are contained within separate compartments.

Surfactants

In one embodiment, the article or composition further contains one or more surfactants. In one embodiment, the article or composition contains a lathering surfactant. What is meant by a lathering surfactant is a surfactant that generates lather when combined with water and mechanically agitated. In one embodiment, the lathering surfactant has an initial foam height reading of at least about 20 mm, such as at least about 50 mm, in the Standard Test Method for Foaming Properties of Surface-Active Agents D1173-53 Set forth in the ASTM Annual Book of ASTM Standards 1001 Section 15 Volume 15.04 (using a concentration of 5 grams per liter, temperature of 49° C., and water hardness of 8 grains per gallon). Examples of lathering surfactants include, but are not limited to, anionic, nonionic, cationic, and amphoteric lathering surfactants.

Nonlimiting examples of anionic lathering surfactants include those selected from the group consisting of sarcosinates, sulfates, isethionates, taurates, phosphates, lactylates, and glutamates. Specific examples include, but are not limited to, sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Nonlimiting examples of nonionic lathering surfactants include alkyl glucosides, alkyl polyglucosides, polyhydroxy fatty acid amides, alkoxylated fatty acid esters, lathering sucrose esters, amine oxides, and mixtures thereof. Specific examples include, but are not limited to, nonionic surfactants such as C8–C14 glucose amides, C8–C14 alkyl polyglucosides, sucrose cocoate, sucrose laurate, lauramine oxide, cocoamine oxide, and mixtures thereof.

Nonlimiting examples of amphoteric lathering surfactants (which also includes zwitterionic lathering surfactants) are betaines, sultaines, hydroxysultaines, alkyliminoacetates, iminodialkanoates, aminoalkanoates, and mixtures thereof.

Nonlimiting examples of amphoteric surfactants of the present invention include disodium lauroamphodiacetate, sodium lauroamphoacetate, cetyl dimethyl betaine, cocoamidopropyl betaine, cocoamidopropyl hydroxy sultaine, and mixtures thereof.

Bulking Agents

In one embodiment, the composition or article further contains a bulking agent. Examples of bulking agents include, but are not limited to, talc, clays such as aluminum silicates, cellulose pulps, silicas, and starches such as corn starch. Other bulking agents are disclosed on pages 1625–26 of the INCI Handbook. The amount of bulking agent in the composition may range from about 5% to about 99.5%, by weight, of the composition.

Cosmetically Active Agents

In one embodiment, the composition or article further contains a cosmetically active agent(s). What is meant by a "cosmetically active agent" is a compound (e.g., a synthetic compound or a compound isolated from a natural source) that has a cosmetic or therapeutic effect on the skin, mucosa, teeth, hair, or nails, including, but not limited to, lightening agents, darkening agents such as self-tanning agents, anti-acne agents, shine control agents, anti-microbial agents, anti-inflammatory agents, anti-mycotic agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, firming agents, anti-callous agents, and agents for hair, nail, mucosa, teeth, and/or skin conditioning.

In one embodiment, the agent is selected from, but not limited to, hydroxy acids, benzoyl peroxide, sulfur resorcinol, ascorbic acid, D-panthenol, hydroquinone, octyl methoxycinnimate, titanium dioxide, octyl salicylate, homosalate, avobenzone, polyphenolics, carotenoids, free radical scavengers, spin traps, retinoids such as retinol and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys and coenzyme Q10, lipoic acid, amino acids such a proline and tyrosine, vitamins, lactobionic acid, acetyl-coenzyme A, niacin, riboflavin, thiamin, ribose, electron transporters such as NADH and FADH2, and other botanical extracts such as aloe vera and legumes such as soy beans, and derivatives and mixtures thereof. The cosmetically active agent will typically be present in the composition or article of the invention in an amount of from about 0.001% to about 20% by weight of the composition, e.g., about 0.01% to about 10% such as about 0.1% to about 5%.

Examples of vitamins include, but are not limited to, vitamin A, a vitamin B such as vitamin B3, vitamin B5, and vitamin B12, vitamin C, vitamin K, and vitamin E and derivatives thereof.

Examples of hydroxy acids include, but are not limited, to glycolic acid, lactic acid, malic acid, salicylic acid, citric acid, and tartaric acid. See, e.g., European Patent Application No. 273,202.

Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis. Other examples of antioxidants may be found on pages 1612–13 of the INCI Handbook.

Anti-Acne Agent

In one embodiment, the article or composition of the present invention includes an anti-acne agent(s). What is meant by an "anti-acne agent" is a drug product effective is the treatment of acne. Examples of anti-acne agents include, but are not limited to, azelaic acid, clindamycin, adapalene, erythromycin, sodium sulfacetamide, retinoic acid, benzoyl peroxide, sulfur, and salicylic acid.

In one embodiment, the article or composition includes about 0.1 to about 50 percent, by weight, of the at least one anti-acne agents, e.g., about 0.5 to about 30 percent, by weight, such as about 0.5 to about 15 percent, by weight, of the at least one anti-acne agent.

In one embodiment, the composition further contains a natural extract to enhance the anti-acne efficacy of the anti-acne agent. Examples of such extracts include, but are not limited to, angelica archangelica root extract, dandelion extract, turmeric extract, and melia azadirachta leaf extract.

pH Adjusters

As the reducing agents and oxidizing agents often exhibit alkaline pH values in the range of from about 9 to about 11 when dissolved in water, the resulting solution created after the exothermic reaction is complete would leave an alkaline pH to the surface being exposed to the agents, which for example could be damaging (e.g., to the stratum corneum). Thus, in one embodiment, the substrate contains an acid or buffering agent (e.g., citric acid) to maintain the pH of the solution created by wetting the composition or article to be in the range of from about 6 to about 8 (e.g., from about 6.5 to about 7.5).

Other Materials

Various other materials may also be present in the compositions and articles useful in the subject invention. These include humectants, emollients, chelating agents (e.g., EDTA) and preservatives (e.g., parabens). Examples of such are listed in pp. 1654–62 and 1626, of the INCI Handbook. In addition, the topical compositions useful herein can contain conventional cosmetic adjuvants, such as dyes, opacifiers (e.g., titanium dioxide and zinc oxide), pigments, and fragrances.

Use to Heat the Skin

In one embodiment, the article or the composition of the invention may be used by wetting such article or substrate with water and applying it to the skin or hair of the user (e.g., containing a lathering surfactant for cleansing and/or a cosmetically active agent for delivering such active to the user). The elevated temperature of the article or composition enables more efficient and effective cleansing of greasy substances from the user's skin or hair, as well as more efficient and effective deposition of cosmetically active agents to the user's skin or hair. In one embodiment, it is used to treat acne, blackheads, and/or whiteheads as the heat generated by the substrate would enhance the opening of the pores on the user's skin.

In one embodiment of the present invention, the article or composition is used to absorb water from the user's hair or skin and to provide heat to such surface (e.g., used as a warming towel or body powder after bathing or showering). In one embodiment, the article or composition may further contain one or active cosmetically active agents, humectants, and/or fragrances.

In one embodiment, the substrate of the article is in the shape of a mask to be placed on the face of the user. In yet another embodiment, the article or composition is used to provide heat to the muscles of the user, e.g., as a wet compress, for the treatment of muscle pain. In yet another embodiment, the article or composition is used to relieve menstrual pain and cramps.

In one embodiment, the invention relates to adding (for example by the user) the reducing and oxidizing agents to a substrate prior to use. Examples of such substrates which the user would desire to be warmed by the agents include, but are not limited to, towels and articles of clothing. In one embodiment, the reducing agent and the oxidizing agent are mixed and stored together prior to application. In another embodiment, the oxidizing agent and the reducing agent are stored and applied separately. The agents can be applied to the substrate by various means known in the art. Examples of such methods include, but are not limited to, dispersing them on the substrate in the form of a powder, spraying them on with electrostatically charged air (e.g., to assist in keeping them separate until deposited at the desired location), and mixing them with a volatile solvent, such as ethanol, and spraying them onto the substrate (e.g., using ultrasonic nozzles or by fluidized bed coating methods). The substrate containing the ingredients can then react with the addition of water, e.g., (i) the addition of water to the substrate prior to application to the skin, hair, or teeth or (ii) the absorbence of water on the skin such as perspiration or residual water on the skin or hair following a bath or shower.

In one embodiment, the equivalent ratio of the oxidizing agent(s) to the reducing agent(s) in the composition or article is such that there is an excess amount of the oxidizing agent remaining after the exothermic reaction. The remaining oxidizing agent in the exothermic article can serve as an anti-microbial agent during the application.

Use to Remove Hair

In one embodiment, the equivalent ratio of the oxidizing agent(s) to the reducing agent(s) in the article or composition is such that there is an excess amount of the reducing agent(s). In one embodiment, the equivalent ratio of the reducing agent(s) to the oxidizing agent(s) is from about 1.1:1 to about 10:1. In one embodiment, one or more of the reducing agent(s) is a depilatory agent such as a salt of thioglycolic acid (e.g., glycolates of calcium, sodium, strontium, potassium, ammonium, lithium, magnesium) or sodium sulfide. Such an article is wet prior to application and/or may be applied to the wet skin (e.g., immediately after shower) to remove the hair. The elevated temperature of the article facilitates the depilatory action of such agents. In one embodiment, the pH value for the exothermic depilatory article or composition containing a thioglycolate as a depilatory agent is greater than about pH 10.

In one embodiment, the article has two substrate layers, one of which contains the reducing agent and one which contains the oxidizing agent. The advantage of this dual-layer wipe is that physical separation of the oxidizing agent and reducing agent prevents the premature reaction during storage. The substrates can be bound together using various techniques known in the art such as point bonding or laminating the substrates with heat, glue, or pressure.

Acne Treatment

In one embodiment, the equivalent ratio of the oxidizing agent(s) to the reducing agent(s) in the article or composition is such that there is an excess amount of the oxidizing agent(s) remaining after the exothermic reaction. The remaining oxidizing agent in the exothermic article will serve as anti-acne agent for the skin application. In a further embodiment, the oxidizing agent is benzoyl peroxide. In a further embodiment, adhesives such as polyacrylate/polyacrylic acid polymers, cellulose polymers (e.g., hydroxyl propyl cellulose, hydroxy methylcellulose, and carboxymethylcellulose), and polyvinypyrrolidone, are incorporated onto the substrate that can be affixed to the skin (e.g., on the acne lesion) to treat acne.

Dental Use

In one embodiment, the equivalent ratio of the oxidizing agent(s) to the reducing agent(s) in the article or composition is such that there is an excess amount of the oxidizing agent(s). The excess oxidizing agent in the exothermic article serves as a bleaching agent and/or an anti-microbial agent during dental application. In a further embodiment, the substrate is a sheet (e.g., an adhesive strip for application to one or more teeth) or a tape or string (e.g., for use as a dental floss), one of the oxidizing agent(s) is sodium carbonate peroxide or carbamide peroxide, one of the reducing agent(s) is sodium sulfite, and the exothermic article is used to apply to the user's teeth for whitening and/or antimicrobial benefits.

A string of the present invention can contain multifilament and/or monofilament yarns. Examples of multifilament yarns include, but are not limited to, polyamides such as nylons (e.g., nylon 6 or nylon 6,6), polyolefins such as polyethylene and polypropylene, polyesters such as poly (ethylene terepthalate), and other fiber forming polymers. In one embodiment, the yarn contains nylon 6,6 yarn (DuPont Canada, Mississauqa, Ontario, as Type 769, with 630 denier and 210 filaments with tenacity of 7–8 gm/denier). Examples of monofilament yarns include, but are not limited to, fluorinated polymers such as polytetrafluoroethylene (PTFE), polyesters, polyolefins, polyamides, and block copolymers. In one embodiment, the yarn contains expanded PTFE with a denier of 900–2000, thickness of 28 to 100 microns and tenacity of 2–3 g/d.

The yarn or tape may be coated with a binding agent that contains a water-insoluble wax, such microcrystalline wax, to which the reducing agent(s), oxidizing agent(s), flavor(s), and any additives may be added. An example of such a binding agent is Multiwax W-445 made by Petroleum Specialties Group of Witco Corporation of New York, N.Y. Examples of flavors include, but are not limited to, natural or synthetic flavor oils such as peppermint, spearmint, cinnamon, fruit and wintergreen flavors that can be obtained from Quest International (Mount Olive, N.J.) International Flavor and Fragrances (Dayton, N.J.), or Virginia Dare (Brooklyn, N.Y.). In one embodiment, the flavor is encapsulated or supported on a carrier such as starch or modified starch.

A whitening sheet can be prepared from a water insoluble polymer film in the shape of a strip to fit on the teeth that is coated on one side with one or more hydrophilic polymers containing the oxidizing and reducing agents. When the strip is applied to stained teeth, the polymer coating will stick to the teeth surface and the saliva will activate the reaction between the reducing and oxidizing agents to generate heat that will whiten the stains on and between teeth. In one embodiment, the hydrophilic polymer is an adhesive, water-soluble polymer. Non-limiting examples of water-soluble polymers with adhesive properties include polyethylene oxides, polyvinyl alcohols, cellulose ethers, and polyvinylpyrrolidones. Such polymers provide adhesion between the whitening strip and the tooth surfaces during the application.

Examples of oxidizing agents that may be incorporated within the string, tape or sheet include calcium peroxide, magnesium peroxide, carbamide peroxide, sodium carbonate peroxide, and combination thereof. Examples of reducing agents that can be added to the string, tape, or sheet include sodium thiosulfate, thiourea, sodium sulfite, sodium bisulfite, sodium borohydride, sodium hypophosphite, ascorbates, and combinations thereof. Other additives that can be added to the string, tape, or sheet include, but are not limited to: dentifrices such as fluoride or fluoride containing compounds such as sodium fluoride and potassium fluoride, and acid phosphates such as disodium phosphate; tooth acidulating agents such as phosphofluoride; tartar control agents such as tetrasodium pyrophosphates; and other pharmacologically active agents.

Upon applying the sheet to the teeth or flossing with the tape, or string, the oxidizing and reducing agents are activated by the saliva present in the oral cavity to generate heat that can assist in whitening the stains on the teeth. In order to initiate the reaction faster on the string, or tape, in one embodiment, a water soluble binder is used such as polyethylene glycol (e.g, PEG 3350 from Union Carbide).

Means of making teeth whitening strips and dental flosses are well known in the art. See, e.g., U.S. patent application No. 20020061329, US 20020012685, and US 20020006388, and U.S. Pat. Nos. 5,645,428, 5,713,738, 6,254,388, 6,162,055, 5,891,453, 5,894,017, 6,096,328, and 5,989,569, and 6,045,811.

Anti-Microbial Bandage

In yet another embodiment, the article is a bandage, e.g., an adhesive bandage, where the equivalent ratio of the oxidizing agent(s) to the reducing agent(s) in the article is such that there is an excess amount of the oxidizing agent(s) remaining after the exothermic reaction. Nonlimiting exemplary reducing agents include ascorbic acid or sodium ascorbate. Upon applying such bandage to a wet skin with a wound (e.g., immediately after rinsing), the moisture will activate the heating process, releasing peroxide to exert an antimicrobial action.

Packaging of Article

In one embodiment, multiple articles are stored within a water-tight container. In another embodiment, the articles are individually wrapped in a water-impermeable film such as those made of polyethylene or polypropylene, for example to form a pouch or envelope containing the article.

EXAMPLES

The following is a description of the manufacture of compositions and articles of the present invention. Other compositions and articles of the invention can be prepared in an analogous manner by a person of ordinary skill in the art.

Example 1

Sodium Sulfite/Sodium Carbonate Peroxide Composition

Sodium sulfite and sodium carbonate peroxide (FB grade) were obtained from EM Science (Gibbstown, N.J. USA) and Solvay Interox (Houston, Tex. USA), respectively. The powders were mixed in different ratios and dispersed into a 35 ml beaker of water at 25° C. Table I summarizes the three compositions used in this example. The final temperature of the product varied from about 45° C. to 80° C., based on the amount of peroxide in the system.

TABLE I

| COMPOSITION NO. | SODIUM SULFITE (G) | SODIUM CARBONATE PEROXIDE (G) | TEMPERATURE (° C.) |
|---|---|---|---|
| 1 | 2.82 | 2.2 | 46 |
| 2 | 2.82 | 3 | 50 |
| 3 | 2.82 | 8.75 | 78 |

Example 2

Sodium Sulfite/Sodium Carbonate Peroxide/Poly(ethylene glycol) Wipe

Powdered blends of sodium sulfite and sodium carbonate peroxide were dispersed in 3 g of molten PEGs and were poured uniformly on the nonwoven substrate. The nonwoven substrate was an 18 in$^2$ substrate of Jacob Holen Nonwoven Product #92016T/01 (Soultz, France) which is a 100% polyethylene terephthalate having a basis weight of 75 grams per m$^2$. Upon cooling, the PEG crystallized to a solid state and thereby encapsulated the powdered mixture. Different grades of PEG (1450, 3350, and 50/50 blend of 1450 and 3350 purchased from Union Carbide) were used for this example. Table II summarizes the compositions used for this example. When approximately 10 ml water at 25 C. was added to these articles, the maximum temperature rise varied from 40 to 45 C. based on the amount and type of PEG. Temperature was measured by placing a thermometer on the surface of the wipe. PEG 1450 worked most efficiently as it dissolved in water in a short time to provide the warming effect.

TABLE II

| COMPOSITION NO. | SODIUM SULFITE (G) | SODIUM CARBONATE PEROXIDE (G) | PEG GRADE (G) | TEMPERATURE (° C.) |
|---|---|---|---|---|
| 4 | 0.91 | 0.97 | 1450 (3) | 45 |
| 5 | 0.91 | 0.97 | 1450/3350 (1.5/1.5) | 40 |
| 6 | 0.91 | 0.97 | 3350 (3) | 42 |

Example 3

Sodium Sulfite and Carbamide Peroxide Wipe

Carbamide peroxide was obtained from Sigma-Aldrich (St. Louis, Mo., USA). Sodium sulfite and carbamide peroxide were mixed and dispersed on the same nonwoven substrate used in Example 2. Table III summarizes two compositions (compositions 7 and 8) used to make the article. Upon the addition of 10 ml of water to the wipe, the temperature rose from 25° C. to 42° C. and 51° C., respectively, for Compositions 7 and 8.

Example 4

Sodium Bisulfite and Sodium Carbonate Peroxide Wipe

Sodium bisulfite, obtained from EM Sciences (Gibbstown, N.J. USA), and sodium carbonate peroxide were mixed in different ratios (Compositions 9 and 10) as summarized in Table III and dispersed on the same nonwoven substrate used in Example 2. Upon the addition of 10 ml of water, the temperature rose from 25° C. to 45° C. and 55° C., respectively, for Compositions 9 and 10.

Example 5

Thiourea and Carbamide Peroxide Wipe

Composition 11 in Table III is a blend of thiourea and carbamide peroxide. The mixture was dispersed on the same nonwoven substrate used Example 2. Upon the addition of 10 ml of water, the temperature rise for this sample was from 25° C. to up to 60° C.

TABLE III

| COMPOSITION NO. | 7 | 8 | 9 | 10 | 11 |
|---|---|---|---|---|---|
| REDUCING AGENTS | | | | | |
| Sodium Sulfite (g) | 1.54 | 3 | | | |
| Sodium Bisulfite (g) | | | 2.47 | 3.71 | |
| Thiourea (g) | | | | | 0.7 |
| OXIDIZING AGENTS | | | | | |
| Carbamide Peroxide (g) | 4.24 | 8.5 | | | 8.56 |
| Sodium Carbonate Peroxide (g) | | | 2.2 | 3.3 | |
| TEMPERATURE (° C.) | 42 | 51 | 45 | 55 | 60 |

Example 6

Prototype Using Sodium Sulfite/Sodium Carbonate Peroxide System

Table IV summarizes a wipe using the oxidizing and reducing agents in conjunction with other powdered additives added on to the same nonwoven substrate used in Example 2. The temperature of this prototype rose from 25° C. to about 50° C. following the addition of 10 ml of water.

TABLE IV

| INGREDIENT | TRADE NAME | SUPPLIER | WEIGHT (g) | % W/W |
|---|---|---|---|---|
| Sodium Sulfite | Sodium Sulfite | EM Sciences, Gibbstown, NJ USA | 2.82 | 30.26 |
| Sodium Carbonate Peroxide | Sodium Carbonate Peroxide | Solvay Interox, Houston, TX USA | 3 | 32.19 |
| Sodium Cocoyl Isethionate | Jordapon CI | BASF, Washington, NJ USA | 0.25 | 2.68 |
| Sodium Lauryl Sulfate | Stepanol WA-100 | Stepan, Northfield, IL USA | 0.25 | 2.68 |
| Silica | Sylloid 2400 | Grace Davison, Baltimore, MD USA | 1 | 10.73 |
| Encapsulated Fragrance | Fragrance 2305-BE | IFF, New York, NY | 0.5 | 5.36 |

TABLE IV-continued

| INGREDIENT | TRADE NAME | SUPPLIER | WEIGHT (g) | % W/W |
|---|---|---|---|---|
| Citric Acid | Citric Acid | Hoffman La Roche, Nutley, NJ | 1.5 | 16.1 |
| TOTAL | | | 9.32 | 100 |

Example 7

Formulations Using Sodium Carbonate Peroxide and Sodium Sulfite

Amounts of the ingredients of Example 6 were varied to determine the effect on temperature change when added directly to water. A mixture of 0.10 g Sodium Sulfite and 0.10 g Sodium Carbonate Peroxide in 10 ml water resulted in a temperature rise of from 25° C. to 28° C. A mixture of 5.60 g Sodium Sulfite and 6.0 g Sodium Carbonate Peroxide in 40 ml water resulted in a temperature rise from 25° C. to 85° C. A mixture of 6.00 g Sodium Sulfite and 6.00 g Sodium Carbonate Peroxide in 35 ml water resulted in a temperature rise from 25° C. to 88° C.

In addition, when calcium peroxide or magnesium peroxide were substituted for sodium carbonate peroxide in the formulation of Example 6, the temperature change was more modest, likely due to their low solubility in water.

Example 8

Heating Body Powder

The body powder of Table V was prepared utilizing sodium sulfite and sodium carbonate peroxide. Three grams of this powder increased the temperature of 10 ml of water from about 20° C. about 34° C.

TABLE V

| INGREDIENT | TRADE NAME | SUPPLIER | WEIGHT (g) | % W/W |
|---|---|---|---|---|
| Sodium Sulfite | Sodium Sulfite | EM Sciences, Gibbstown, NJ USA | 5.64 | 11.28 |
| Sodium Carbonate Peroxide | Sodium Carbonate Peroxide | Solvay Interox, Houston, TX USA | 6.00 | 12 |
| Cornstarch | Cornstarch 034500 | Corn Products, Summit-Argo, IL | 15.91 | 31.82 |
| Talc | Windsor Talc Grade 66 | Luzenac America, Englewood, CO | 15.415 | 30.83 |
| Sodium Bicarbonate | Sodium Bicarbonate USP 3 | Church & Dwight, Princeton, NJ | 3.535 | 7.07 |
| Tribasic Calcium Phosphate, N. F. | Tribasic Calcium Phosphate | Rhodia, Cranberry, NJ | 0.18 | 0.36 |
| Fragrance | 3324-BD | IFF, New York, NY | 0.18 | 0.36 |
| Encapsulated Fragrance | Fragrance LF0-06 | IFF, New York, NY | 0.14 | 0.28 |
| Citric Acid | Citric Acid | Hoffman La Roche, Nutley, NJ | 3 | 6 |
| TOTAL | | | 50.0 | 100 |

Example 9

Depilatory Wipe

A depilatory wipe can be prepared containing the ingredients set forth in Table VI.

TABLE VI

| INGREDIENT | SUPPLIER | WEIGHT (g) |
|---|---|---|
| PART A | | |
| Calcium thioglycolate, trihydrate | Spectrum Laboratory Product, Inc. Gardena, CA 90248 | 15–30 |
| Calcium carbonate, light powder, USP | Spectrum Laboratory Product, Inc. Gardena, CA 90248 | 15 |
| Calcium hydroxide, USP | Spectrum Laboratory Product, Inc. Gardena, CA 90248 | 1.5 |
| Encapsulated Fragrance (Trade name: Fragrance LF0-06) | IFF, New York, NY | 0.5 |
| Propylene glycol, USP | Spectrum Laboratory Product, Inc. Gardena, CA 90248 | 5–20 |
| PART B. | | |
| Sodium carbonate peroxide | Solvay Interox, Houston, TX | 5 |
| Propylene glycol, USP | Spectrum Laboratory Product, Inc. Gardena, CA 90248 | 5 |

All the ingredients, except the encapsulated fragrance and propylene glycol, are ground individually to fine powder prior to wipe preparation. The ingredients in PART A are thoroughly mixed and uniformly applied to a nonwoven substrate sheet of 500 cm$^2$. The ingredients in PART B are uniformly applied to another nonwoven substrate sheet of 500 cm$^2$ (Sheet B). The Sheets A and B are then over-layered and point bonded to form a depilatory wipe.

Example 10

Heating Dental Floss

Yarn is unwound from the supply roll and passed into a heated bath (90° C.) containing the ingredients set forth below in Table VII. The yarn is then passed through a chilled tunnel (3° C.) and rewound onto a take-up roll. The total coating weight may be varied from about 10 percent to about 50 percent by weight based on the weight of the uncoated yarn.

TABLE VII

| INGREDIENT | (W/W %) | TRADENAME/SUPPLIER |
|---|---|---|
| Microcrystalline wax | q.s. | Multiwax W-445 Petrolatum Specialties Group of Witco Corporation, New York, NY |
| Flavor | 15% | Quest International Mount Olive, NJ |
| Sodium Saccharin | 1% | Syncal S Powder PMC Specialties Cincinnati, OH |
| Sodium Carbonate Peroxide | 7–15% | FB Grade Solvay Interox Houston, TX |

TABLE VII-continued

| INGREDIENT | (W/W %) | TRADENAME/SUPPLIER |
|---|---|---|
| Sodium Sulfite | 5% | EM Sciences Gibbstown, NJ |

Example 11 eating Dental Strip

A dental strip is made using a coating that is made from molten polyethylene glycol (PEG) containing about 20% (w/w) of carbamide peroxide and about 5% (w/w) sodium sulfite. The molten composition is then coated at a thickness of about 1 mm onto a polyethylene film of thickness of about 1 mm at about 60° C. using conventional coating equipment. Upon cooling, a thin composite structure is formed. When the PEG coated side is applied to teeth surface, the saliva from the oral cavity will activate the reaction between the agents to generate heat. This heat and the excess sodium carbonate peroxide will assist in whitening the teeth surface. The polyethylene film can be removed after the temperature returns to ambient condition. This process can be repeated until the desired whitening of the teeth is achieved.

Example 12

Heating Adhesive Dental Strip

A dental strip is made using a coating that is made from molten polyethylene glycol (PEG) containing about 20% (w/w) of sodium carbonate peroxide, about 5% (w/w) sodium sulfite, and about 20% polyvinylpyrrolidone (PVP, Plasdone® Povidone K-29/32 USP, ISP, Wayne, N.J.). Citric acid can be added to adjust the pH to about 7. The molten composition is then coated at a thickness of about 1 mm onto a polyethylene film of thickness of about 1 mm at about 60° C. using conventional coating equipment. Upon cooling, a thin composite structure is formed. When the PEG/PVP coated side is applied to teeth surface, the saliva from the oral cavity will activate the reaction between the agents to generate heat. This heat and the excess sodium carbonate peroxide will assist in whitening the teeth surface. The adhesive whitening strip can be removed after a pre-determined time period (e.g., that may vary from about 5 minutes to about 30 minutes). This process can be repeated periodically until the desired whitening of the teeth is achieved.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of removing hair from the skin, said method comprising applying to said hair a substantially dry article comprising an insoluble substrate, at least one oxidizing agent, and at least one reducing agent, wherein at least one of said at least one reducing agent is a depilatory agent, the equivalent ratio of said at least one oxidizing agent to said at least one reducing agent is less than 1:1, and said article is exothermic when wet with water and, wherein said article is wet with water prior to, during, or after said application.

2. The method of claim 1 wherein said substrate comprises a nonwoven sheet.

3. The method of claim 1 wherein said at least one oxidizing agent comprises at least one compound selected from the group consisting of sodium perborate monohydrate, ammonium persulfate, sodium persulfate, potassium persulfate, sodium carbonate peroxide, calcium peroxide, magnesium peroxide, and carbamide peroxide.

4. The method of claim 1 wherein said at least one reducing agent comprises a compound selected from the group consisting of thioglycolic acid, thioethylene glycol, thioglycerol, thioethanol, thioactic acid, thiosalicylic acid, L-cysteine, D-cysteine, DL-cysteine, N-acetyl-L-cysteine, DL-homocysteine, N-carbamoyl cysteine, glutathion, cysteamine, salts and esters thereof, and sulfide salts.

5. The method of claim 3 wherein said at least one reducing agent comprises a compound selected from the group consisting of thioglycolic acid, thioethylene glycol, thioglycerol, thioethanol, thioactic acid, thiosalicylic acid, L-cysteine, D-cysteine, DL-cysteine, N-acetyl-L-cysteine, DL-homocysteine, N-carbamoyl cysteine, glutathion, cysteamine, salts and esters thereof, and sulfide salts.

6. The method of claim 3 wherein said at least one reducing agent comprises a compound selected from the group consisting of thioglycolic acid and salts and esters thereof.

7. The method of claim 1 wherein the equivalent ratio of said at least one oxidizing agent to said at least one reducing agent ranges from 1:1.5 to 1:10.

8. The method of claim 1 wherein following being wet with water, a surface of said article becomes heated to from about 30° C. to about 50° C.

9. The method of claim 1 said article further comprising a water-soluble polymer in contact with said at least one oxidizing agent, said at least one reducing agent, or both said at least one oxidizing agent and said at least one reducing agent.

10. The method of claim 9 wherein said water-soluble polymer is selected from the group consisting of polyethylene glycol, polyethylene oxide, polyvinyl alcohol, cellulose ethers, polyvinylpyrrolidone, copolymers of vinylpyrrolidone, and mixtures thereof.

11. A method of removing hair from the skin, said method comprising wetting a composition with water prior to, during, or after application of said composition to said hair, wherein said composition comprises at least one oxidizing agent and at least one reducing agent, at least one of said at least one reducing agent is a depilatory agent, the equivalent ratio of said at least one oxidizing agent to said at least one reducing agent is less than 1:1, and said composition is exothermic when wet with water.

12. The method of claim 11 wherein said composition is applied to a substrate prior to application to the skin.

13. The method of claim 11 wherein said at least one oxidizing agent comprises at least one compound selected from the group consisting of sodium perborate monohydrate, ammonium persulfate, sodium persulfate, potassium persulfate, sodium carbonate peroxide, calcium peroxide, magnesium peroxide, and carbamide peroxide.

14. The method of claim 11 wherein said at least one reducing agent comprises a compound selected from the group consisting of thioglycolic acid, thioethylene glycol, thioglycerol, thioethanol, thioactic acid, thiosalicylic acid, L-cysteine, D-cysteine, DL-cysteine, N-acetyl-L-cysteine, DL-homocysteine, N-carbamoyl cysteine, glutathion, cysteamine, salts and esters thereof, and sulfide salts.

15. The method of claim 13 wherein said at least one reducing agent comprises a compound selected from the group consisting of thioglycolic acid, thioethylene glycol, thioglycerol, thioethanol, thioactic acid, thiosalicylic acid, L-cysteine, D-cysteine, DL-cysteine, N-acetyl-L-cysteine, DL-homocysteine, N-carbamoyl cysteine, glutathion, cysteamine, salts and esters thereof, and sulfide salts.

16. The method of claim 13 wherein said at least one reducing agent comprises a compound selected from the group consisting of thioglycolic acid and salts and esters thereof.

17. The method of claim 11 wherein the equivalent ratio of said at least one oxidizing agent to said at least one reducing agent ranges from 1:1.5 to 1:10.

18. The method of claim 11 wherein following being wet with water, a surface of said article becomes heated to from about 30° C. to about 50° C.

19. The method of claim 11 said article further comprising a water-soluble polymer in contact with said at least one oxidizing agent, said at least one reducing agent, or both said at least one oxidizing agent and said at least one reducing agent.

20. The method of claim 19 wherein said water-soluble polymer is selected from the group consisting of polyethylene glycol, polyethylene oxide, polyvinyl alcohol, cellulose ethers, polyvinylpyrrolidone. copolymers of vinylpyrrolidone, and mixtures thereof.

* * * * *